(12) United States Patent
Pirotte et al.

(10) Patent No.: US 6,447,747 B1
(45) Date of Patent: Sep. 10, 2002

(54) PROCESS FOR THE PREPARATION OF RADIOPHARMACEUTICALS

(75) Inventors: Robert Jean Marie Denis Pirotte, Tongrinne (BE); David Peter Nowotnik, Kingsville, MD (US); Brian Fredrick Abeysekera, St. Burnaby (CA)

(73) Assignee: Guilford Pharmaceuticals Inc., Baltimore, MD (US)

( * ) Notice: Subject to any disclaimer, the term of this patent is extended or adjusted under 35 U.S.C. 154(b) by 0 days.

(21) Appl. No.: 08/959,028

(22) Filed: Oct. 28, 1997

Related U.S. Application Data

(63) Continuation-in-part of application No. 08/739,381, filed on Oct. 29, 1996, now abandoned.

(51) Int. Cl.$^7$ .......................... A61K 51/00; A61M 36/14
(52) U.S. Cl. .................... 424/1.85; 546/124; 424/1.11; 424/1.65
(58) Field of Search ............................. 424/1.11, 1.37, 424/1.85, 1.65, 1.81; 546/124, 125, 127

(56) References Cited

U.S. PATENT DOCUMENTS

| | | | |
|---|---|---|---|
| 5,077,035 A | | 12/1991 | Wieland et al. |
| 5,213,787 A | | 5/1993 | Wilbur et al. |
| 5,413,779 A | | 5/1995 | Kuhar et al. |
| 5,439,666 A | * | 8/1995 | Neumeyer et al. ......... 424/1.85 |
| 5,480,631 A | | 1/1996 | De Paulis et al. |
| 5,720,935 A | * | 2/1998 | Kassis et al. .............. 424/1.73 |

OTHER PUBLICATIONS

Zea–Ponce (1994), Appl. Radiat. Isot., vol. 45, No. 1, pp. 63–68, "Formation of 1–[$^{123}$I] Iodobutane In Labeling [$^{123}$I] Iomazenil By Iododestannylation: Implication For The Reaction Mechanism," 1994.*

Baldwin (1993), Nucl. Med. Biol. vol. 20, No. 5, pp. 597–606, "Evaluation Of The Monoamine Update Site Ligand [$^{123}$I] Methyl 3β–(4–Iodophenyl)–Tropene 2β–Carboxylate ([$^{123}$I] β–CIT) In Non–Human Primates: Pharmacokinetics, Biodistribution And SPECT Brain Imaging Coregistered With MRI", 1993.*

Malison Et Al (Dec. 1995), The Journal Of Nuclear Medicine, vol. 36, No. 12, pp. 2290–2297, "Striatal Dopamine Transporter Imaging In Nonhuman Primates With Iodine–R3 IPT SPECT", Dec. 1995.*

Cohen Et Al (1995), Nucl. Med. Biol., vol. 22, No. 8, pp. 977–984, "N.C.A. Radio Synthesis Of [123,124 I] β–CIT, Plasma Analysis And Pharmacokinetic Studies With SPECT And PET", 1995.*

Carrol (1991) Med. Chem. Res, vol. 1, pp. 289–294, "[$^{123}$I] 3β–(4–Iodophenyl) Tropan–2β–Carboxylic Acid Methyl Ester (RTI–55): A Unique Cocaine Receptor Ligand For Imaging The Dopamine And Serotonin Transporters In Vivo", 1991.*

Zea–Ponce (1995), J. Nucl–Med. vol. 36, No. 1, pp. 525–529, Simplified Multidose Preparation Of Iodine–123–β–CIT: A Marker For Dopamine Transporters, Mar. 1995.*

Holum (1995), Ninth Edition, Elements Of General, Organic, And Biological Chemistry, pp. 42–44 "Periodic Law And Periodic Table", 1995.*

Goodman Et Al (1994), J. Med. Chem, vol. 37, No. 10, pp. 1535–1542, Synthesis And Characterization of Radioiodinated N–(3–Iodopropen–1–YL)–2β–Carbomethoxy–3β–(4,–Chlorophenyl) Tropanes: Potential Dopamine Reuptake Site Imaging Agents, 1994.*

Angelberger Et Al (1995), Radioactive Isotopes In Clinical Medicine And Research Advances In Pharmacological Science, "Optimized Preparation Of The Dopaminergic Receptor Ligands 123I–Epidepride And $^{123}$I–CIT", 1995.*

Kuikka Et Al (1995), Eur. J. Nucl. Med., vol. 22, No. 4, pp. 356–360, "Comparison Of Iodine–123, Labeled 2β–Carbomethoxy 3β–(4–Iodophenyl) Tropane And 2β–Carbomethoxy–3β–(4–Iodophenyl)–N–(3–Fluoropropyl) Nortropane For Imaging Of The Dopamine Transporter In The Living Human Brain," Apr. 1995.*

* cited by examiner

Primary Examiner—Dameron L. Jones
(74) Attorney, Agent, or Firm—Lyon & Lyon LLP

(57) ABSTRACT

Process for the preparation of radiohalogenated radiopharmaceuticals by an electrophillic substitution, preferably halogenodestannylation reactions, by the reaction of an organometallic substituted precursor, preferably a trialkyl tin substituted precursor, with a radioactive halogen, preferably a radioactive iodine, astatine or bromine composition, in the presence of a catalytically effective amount of an anion selected from the group consisting of bromide, chloride and nitrite anion in an acid medium with an oxidizing agent.

33 Claims, No Drawings

PROCESS FOR THE PREPARATION OF RADIOPHARMACEUTICALS

CROSS-REFERENCE TO RELATED APPLICATIONS

This application is a continuation-in-part of U.S. patent application Ser. No. 08/739,381 filed on Oct. 29, 1996 now abandoned.

FIELD OF THE INVENTION

The present invention relates to a process for the preparation of radiotracers and radiopharmaceuticals, and more particularly to an improved process for preparing radiopharmaceuticals labeled with electrophillic halogens such as radioactive iodine. The present invention specifically relates to halogenodestannylation reactions, in particular iododestannylation reactions, in which the yield is significantly enhanced by the presence of a catalytically effective amount of a bromide, chloride or nitrite anion during the reaction.

BACKGROUND OF THE INVENTION

Radiotracers and radiopharmaceuticals are useful in the diagnosing, studying and monitoring of medical conditions and the uptake of pharmaceutical compositions. Some radiopharmaceuticals have therapeutic indications. Of particular interest are those pharmaceutical compositions that block access to or are taken up by the receptor binding agents for dopamine transporters/cocaine receptor binding sites.

Radiopharmaceuticals that bind to the dopamine transporter/cocaine receptor binding sites have a variety of potential uses. Because of the unique anatomical location of the dopamine transporter/cocaine receptor binding sites, a high affinity probe for imaging of these sites in vivo in the brain may be carried out using, for example, positron emission tomography (PET) or single photon emission computed tomography (SPECT). Thus, potential uses include imaging probes for dopamine transporter/cocaine binding sites, imaging probes for neurodegenerative disorders, monitoring means for drug therapies for cocaine abuse and monitoring means for drug therapies for neurodegenerative disorders such as Parkinson's disease.

The imaging probes for the dopamine transporter/cocaine receptor binding sites are useful for the purposes of (i) assaying cocaine receptors in chronic cocaine users and in individuals exposed to cocaine prenatally, (ii) assaying the receptor occupancy of potential cocaine therapeutics, and (iii) assaying cocaine receptors in individuals that abuse other drugs. Such imaging is also useful for monitoring the occupancy of the dopamine transporter by established and novel drugs that are targeted to and/or bind to these sites; these drugs include, but are not limited to, antidepressants (e.g., bupropion), attention deficit disorder/hyperactivity syndrome therapies (e.g., methylphenidate or pemoline), and dopamine uptake inhibitors useful for treating Parkinson's disease (e.g., benztropine, also termed cogentin).

Additionally, such imaging agents are useful for diagnosing or monitoring various central nervous system (CNS) disorders and neuropsychiatric disorders that involve dopamine transporters such as Parkinson's disease, a neurological disorder characterized by the degeneration of dopamine nerve terminals; Alzheimer's disease; schizophrenia and Tourette's syndrome. These imaging agents can be used to compare resultant image densities in normal and disease states and use the observed changes associated with these diseases as indicators diagnostic of diseased states. For example, in Parkinson's disease, there is a degeneration of dopaminergic nerve terminals in basal ganglia; the degeneration of these nerve terminals result in a loss of dopamine transporters in this region and this loss could be detected by imaging dopaminergic transporters. These imaging agents can also be employed to determine progression of the disease and/or prognosis as to various treatment regimes.

Finally, radiopharmaceuticals can be used to screen for drugs that would have a high affinity at serotonin transporters or dopamine transporters. Serotonin transporters are important in that they are a target for antidepressant drugs. Radio-labeled ligands can be used in screening studies to identify potentially new useful antidepressant drugs and to identify compounds that could be transported by or into various nerve terminals and be neurotoxic.

Therefore, stable, radiolabeled ligands, i.e., radio-labeled tracers and radiopharmaceuticals, suitable for visualizing and measuring changes of these sites in vivo in conjunction with functional imaging, such as positron emission tomography (PET) or single photon emission computed tomography (SPECT), are valuable tools for the diagnosis and treatment of neurodegenerative diseases associated with dopaminergic neurons as well as the monitoring of cocaine addiction treatments. Such functional imaging techniques provide information about the location, number, and size of specific neurological phenomena. Moreover, the ability to monitor changes of the dopamine (DA) transporter with optimal radioligands in the human brain may enable diagnosis and monitoring of the CNS consequences associated with cocaine abuse.

Radiolabelling of these cocaine derivatives and analogues, and other ligands that bind to the neuronal dopamine and serotonin reuptake transporters has been achieved by several methods. Preferred methods in the prior art have included radioiodination procedures by non-isotopic exchange on the bromo-analogue (nucleophilic non-isotopic iodo-for-bromo exchange) and iododestannylation of a trialkyltin or trialkylstannyl precursor. Of these methods, iododestannylation has been preferred as a means for preparation of aromatic radioiodinated tracers relatively rapidly with relatively high yield and specific activity.

Although good to high yields of radiolabeled pharmaceuticals have been reported in the literature, this has been for small scale batch preparation of approximately 1 to 5 patient doses per batch with a relatively low radioactivity, on the order of 10 mCi, associated with the radiolabel. However, we have discovered that when attempts are made to scale up production to at least 25 to 35 patient doses per batch, not only does the yield drop significantly, but side reactions become significant leading to the presence of undesired byproducts in the resultant product. Thus, the prior art process have lower yields that are produced at a greater cost and longer time due to the additional purification steps required.

Part of the problem with scale up to commercial levels may be associated with or attributed to the use of a radiolabel with higher activity. At small scale production, the radiolabeled pharmaceutical is used shortly after it is made. With larger scale production, a longer time elapses before the radiopharmaceutical is used, thus necessitating radiolabels with higher radioactivity levels on the order of 100 to 150 mCi or greater. However, it is well known in the art that the higher activity levels have a detrimental effect on chemical reactions involving the radiolabel, thus adversely impacting the yield and purity of the resultant product. This adverse effect of higher activity levels is referred to as radiolysis.

Those skilled in the art also believed that a particular problem is associated with the presence of chloride anions and other reactive anions in the iododestannylation process since they may compete with the iodide anion in the halogenodestannylation reaction, thus interfering with the iododestannylation reaction and producing undesired byproducts. As noted above, this effect may become more pronounced at higher activity levels.

Surprisingly, we have discovered that in the presence of a catalyst—particularly a small but catalytically effective amount of a bromide, chloride or nitrite anion—the yield of the iododestannylation chemical reaction significantly improved resulting in considerably purer radiopharmaceutical compositions. The improvement was especially significant when the reaction was conducted with a radiolabel having high amounts of radioactivity on the order of 100mCi to 600mCi, and even greater.

As used herein, the term catalyst refers to an agent, i.e. the bromide, chloride, or nitrite anion, also referred to as a catalytic anion, that brings about a modification, particularly an increase in the yield of the desired reaction product. The term catalytically effective amount refers to an amount sufficient to bring about the increased yields of the present invention. See for example, the differences in yield between Example 1 and Example 2.

SUMMARY OF THE INVENTION

The present invention is directed to an improved process for the preparation of iodine, astatine or bromine labeled radiopharmaceuticals. In particular, the present invention is directed to a process for the preparation of iodine, astatine or bromine labeled radiopharmaceuticals by the reaction of an organometallic substituted precursor, preferably a trialkyl tin substituted precursor, with a radioactive halogen, preferably a radioactive iodine, astatine or bromine composition, in the presence of a catalytically effective, or yield enhancing, amount of a bromide, chloride or nitrite anion. The bromide, chloride or nitrite anion can be derived from any suitable source, and is preferably from KBr, HCl, NaCl, or sodium nitrite.

One embodiment of the present invention is directed to a process for the preparation of a radiopharmaceutical by destannylation of a trialkyl tin substituted precursor with a radioactive halogen composition in the presence of a catalyst selected from the group comprising bromide, chloride and nitrite anions.

Another embodiment is directed to a process for the preparation of, a radiopharmaceutical from a trialkyl tin substituted precursor comprising the steps of forming a solution of said trialkyl tin substituted precursor in a solvent; adding a radioactive halogen composition to the solution of the trialkyl tin substituted precursor; adding a catalytically effective amount of an anion selected from the group comprising bromide, chloride and nitrite anion to the radioactive halogen composition and trialkyl tin substituted precursor solution to form a reaction mixture; acidifying said reaction mixture; adding an oxidizing agent to the acidified reaction mixture and allowing it to react to produce said radiopharmaceutical.

An alternative embodiment of the invention is directed to a method of reducing the effects of radiolysis on the yield of a high activity radiopharmaceutical produced by halogenodestannylation of a trialkyl tin substituted precursor with a high activity radiohalogen, said method comprising the steps of forming a solution of said trialkyl tin substituted precursor in a solvent; adding a high activity radioactive halogen composition to the solution of the trialkyl tin substituted precursor; adding a catalytically effective amount of an anion selected from the group comprising bromide, chloride and nitrite anion to the high activity radioactive halogen composition and trialkyl tin substituted precursor solution to form a reaction mixture; acidifying said reaction mixture; adding an oxidizing agent to the acidified reaction mixture and allowing it to react to produce said high activity radiopharmaceutical wherein said catalytically effective amount of anion reduces the effect of radiolysis and increases the yield of said high activity radiopharmaceutical.

Still another embodiment of the invention is directed to a process for increasing the yield of a radiopharmaceutical prepared by destannylation of a trialkyl tin substituted precursor with a radioactive halogen composition wherein said process is conducted in the presence of a catalyst selected from the group comprising bromide, chloride and nitrite anions.

DETAILED DESCRIPTION OF THE INVENTION

Radiopharmaceuticals and radiotracers can be prepared by substitution reactions which replace an organometallic group on a organometallic substituted precursor with a radioactive halogen. Preferably, the radiopharmaceuticals are prepared by halogenodestannylation reactions, particularly iododestannylation reactions, from a trialkyl tin substituted precursor, where the trialkyl tin group is attached to an unsaturated carbon atom, particularly a vinyl group, benzyl group, phenyl ring or any aromatic ring.

Any suitable pharmaceutical composition can be used to prepare the organometallic substituted precursor. Preferred pharmaceuticals are those capable of acting with dopamine and serotonin receptors, particularly cocaine analogues and derivatives, and which have an unsubstituted carbon atom, such as a vinyl group, benzyl group, phenyl ring or any aromatic ring, to which the radioactive halogen will be attached.

The organometallic or trialkyl tin group is attached to the unsaturated carbon atom through any suitable reaction sequence, and is well known in the art. The preferred organometallic group of the present invention is a trialkyl tin group represented by the following formula:

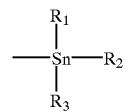

wherein $R_1$, $R_2$, and $R_3$ are independently straight or branched alkyl groups having from one to six carbon atoms, and include methyl, ethyl, n-propyl, isopropyl, n-butyl, sec-butyl, isobutyl, tert-butyl, n-pentyl, n-hexyl, and the like. Particularly preferred trialkyl tin groups include trimethyl stannyl and tributyl stannyl.

The radioactive halogen compound is can be any known radioactive iodine, astatine, or bromine capable of being imaged or traced including, but not limited to, $^{123}I$, $^{124}I$, $^{125}I$, $^{126}I$, $^{127}I$, $^{131}I$, $^{209}At$, $^{210}At$, $^{211}At$, $^{74}Br$, $^{75}Br$, $^{76}Br$, and $^{77}Br$. Particularly preferred radiolabels include $^{123}I$, $^{124}I$, $^{125}I$, $^{131}I$, $^{211}At$, and $^{77}Br$.

The substitution reaction in which the organometallic group is replaced with the radioactive halogen takes place by the addition of radioactive halogen, i.e. radioactive iodine, astatine, or bromine, to a solution of the organometallic substituted precursor in acid medium and in the presence of an oxidizing agent. The acid medium may be prepared from any suitable acid, or combination of acids.

Any suitable oxidizing agent may be used and such oxidizing agents are well known in the art. Preferable oxidizing agents include peracetic acid, chloramine-T and iodogen.

The exact mechanism of the process in which the radioactive iodine, astatine or bromine replaces the organometallic group, i.e. the trialkyl tin group, is not clearly understood, but it is believed that the oxidizing agent generates $X^{\delta+}$ which displaces the organometallic group, i.e. the trialkyl tin group, by an electrophillic mechanism. The reaction is usually complete within a few minutes at room temperature, and is "quenched" by the addition of a base to raise the pH and the addition of a reducing agent to consume all of the remaining oxidizing agent.

As we discovered, the yield of the radiopharmaceutical product resulting from the halogenodestannylation reaction is significantly increased when the reaction is conducted in the presence of a catalytically effective amount of bromide, chloride or nitrite anions, particularly when the reaction is performed with high amounts of radioactivity. Thus, as shown in the examples below, the addition of bromide, chloride or nitrite anion to a reaction mixture with high activity enabled a three to four-fold increase in the yield of the radiopharmaceutical. This effect is particularly pronounced at very high levels of radioactivity on the order of 560 mCi where the effect of the addition of a catalytically effective amount of chloride anion resulted in a thirteen-fold increase in the yield of the radiopharmaceutical as shown in Examples 13 and 14.

The amount of the catalyst anion, i.e. the bromide, chloride or nitrite anion, needed depends upon a variety of factors including bromide, chloride or nitrite composition from which the anion is created, the precursor compound, the alkyl groups on the organometallic substituent, the temperature and pH of the reaction mixture and the like. Preferably, the amount of bromide, chloride or nitrite anion used is from about 0.1 N to about 1.0 N. Suitable bromide, chloride, or nitrite anion sources for use as a catalyst in the process of the present invention must be in a water or organic soluble form.

Preferred bromide anion sources include Group I and Group II metal bromides and transitional metal bromides, particularly HBr, LiBr, NaBr, KBr, $BeBr_2$, $MgBr_2$, $CaBr_2$, $SrBr_2$, $BaBr_2$, $FeBr_3$ and the like. Most preferred bromide anion sources are NaBr and HBr.

Preferred chloride anion sources include Group I and Group II metal chlorides and transitional metal chlorides, particularly HCl, LiCl, NaCl, KCl, $BeCl_2$, $MgCl_2$, $CaCl_2$, $SrCl_2$, $BaCl_2$, $FeCl_3$ and the like. Most preferred chloride anion sources are NaCl and HCl.

Preferred nitrite anion sources include Group I and Group II metal nitrites and transitional metal nitrites, particularly $HNO_2$, $LiNO_2$, $NaNO_2$, $KNO_2$, $Be(NO_2)_2$, $Mg(NO_2)_2$, $Ca(NO_2)_2$, $Sr(NO_2)_2$, $Ba(NO_2)_2$, $Fe(NO_2)_3$ and the like. Most preferred nitrite anion sources include sodium nitrite.

Preferable reactions include a halogenodestannylation a reaction where a trialkyl tin group is attached to a vinyl group, as represented by the reaction depicted below:

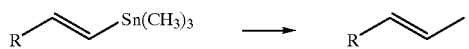

wherein X represents a radioactive halogen, preferably a radioactive iodine, astatine, or bromine;

$R_1$, $R_2$, $R_3$ are independently straight or branched alkyl groups having from one to six carbon atoms; and $R_4$ and the vinyl group together form the pharmaceutical compound.

Other preferable reactions include an halogenodestannylation reaction with a trialkyl tin group attached to a phenyl group. More preferably, the halogenodestannylation reaction is with a trialkyl tin group attached to the phenyl ring of β-CT precursor as shown in the following schematic:

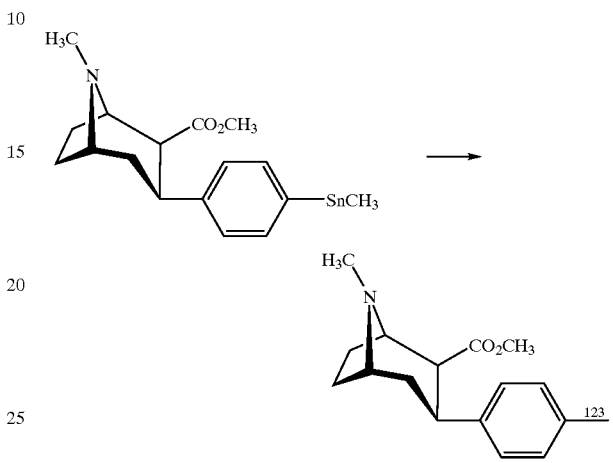

wherein X represents a radioactive halogen, preferably a radioactive iodine, astatine, or bromine.

As noted above, the above reactions take place by the addition of a radioactive halogen, particularly radioactive iodine, astatine, or bromine, to a solution of the trialkyl tin substituted benzyl, phenyl, or vinyl compound in acid medium, in the presence of an oxidizing agent such as peracetic acid, chloramine-T or iodogen.

The preparation of suitable trialkyl tin substituted benzyl, phenyl, or vinyl compounds are well known in the art. The trialkyl tin substituted compound can be dissolved in any suitable solvent such as acetonitrile or ethanol.

The acid medium is formed by lowering the pH using any suitable acid, such as sulphuric acid or acetic acid. The pH should not be so low that the competing protodestannylation reactions occurs in preference to the halogenodestannylation reaction of the present invention.

In the process of the present invention, the yield of the above reaction is significantly increased by the addition of a catalytically effective amount of bromide, chloride or nitrite anion. The catalytic anion, i.e. the bromide, chloride or nitrite anion, is added to the solution of the trialkyl tin substituted compound. The pH of the solution of the chloride anion with the trialkyl tin substituted compound is adjusted to the desired level by adding a suitable acid, and then the oxidizing agent is quickly added. The reaction mixture is stirred or agitated until the reaction is completed, which is within a few minutes at room temperature. The reaction mixture is then "quenched" by the addition of base to raise pH and a reducing agent to consume all of the oxidizing agent.

The present invention is further illustrated by the following examples. All parts and percentages in the examples and throughout the specification and claims are by weight based on a total of 100%, unless otherwise indicated.

The following examples demonstrate that the presence of a small but catalytically effective amount of bromide, chloride or nitrite anion has a beneficial effect on the yield of the desired radiopharmaceutical. The increase in yield is particularly striking at high levels of radioactivity.

EXAMPLE 1

Trimethylstannyl-β-CT (50 μg) was dissolved in acetonitrile (850 μL). 130 mCi of no-carrier-added sodium iodide ($^{123}$I) was diluted to 100 μL with water, and added to a 140 μL aliquot of the solution of trimethylstannyl-β-CT in acetonitrile. To this mixture was added (in sequence) 30 μL of water, 30 μL of 7.2N sulfuric acid and 40 μL of a dilute aqueous solution of peracetic acid (0.04 μL/mL). The mixture was agitated and allowed to react at room temperature for eight minutes, and quenched by the addition of sodium bicarbonate, and sodium bisulfite solutions. The formation of $^{123}$I β-CIT $^{123}$I-3-β-(4-iodophenyl) tropan-2β-carboxylic acid methyl ester, was monitored by thin layer chromatography (ITLC=SG, eluted with ethanol:water:acetic acid, 20:80:2.5 v/v/v). The yield of $^{123}$I β-CIT was 25.8%.

EXAMPLE 2

The procedure described in Example 1 was repeated exactly as described except that the 30 μL of water was replaced by 30 μL of 1.2N aqueous sodium chloride solution. The yield of $^{123}$I β-CIT as determined by the ITLC method was 94.9%.

EXAMPLE 3

The procedure described in Example 1 was repeated exactly as described except that the 30 μL of water was replaced by 30 μL of 0.6N aqueous sodium chloride solution. The yield of $^{123}$I β-CIT as determined by the ITLC method was 91.9%.

EXAMPLE 4

The procedure described in Example 3 was repeated exactly as described except that the reaction time was reduced to one minute. The yield of $^{123}$I β-CIT as determined by the ITLC method was 85%.

EXAMPLE 5

Trimethylstannyl-β-CT (50 μg) was dissolved in acetonitrile (850 μL). 130 mCi of no-carrier-added sodium iodide ($^{123}$I) was diluted to 100 μL with water, and added to a 140 μL aliquot of the solution of trimethylstannyl-β-CT in acetonitrile. To this mixture was added (in sequence) 30 μL of water, 30 μL of 0.61N hydrochloric acid and 40 μL of a dilute aqueous solution of peracetic acid (0.04 μL/mL). The mixture was agitated and allowed to react at room temperature for five minutes, and quenched by the addition of sodium bicarbonate and sodium bisulfite solutions. The formation of $^{123}$I β-CIT was monitored by thin layer chromatography (ITLC=SG, eluted with ethanol:water:acetic acid, 20:80:2.5 v/v/v). The yield of $^{123}$I β-CIT was 97.8%.

EXAMPLE 6

The procedure described in Example 1 is repeated exactly as described except that the 30 μL of water is replaced by 30 μL of 0.1N aqueous sodium hypochlorite solution. The yield of $^{123}$I β-CIT is determined by the ITLC method.

EXAMPLE 7

The procedure described in Example 2 is repeated except that tributylstannyl-β-CT dissolved in ethanol is used instead of trimethylstannyl-β-CT dissolved in acetonitrile.

EXAMPLE 8

The procedure described in Example 2 is repeated except that N-fluoropropyl-trimethylstannyl-β-CT is used instead of trimethylstannyl-β-CT.

EXAMPLE 9

The procedure described in Example 2 is repeated except that N-fluoropropyl-tributylstannyl-β-CT dissolved in ethanol is used instead of trimethylstannyl-β-CT dissolved in acetonitrile.

EXAMPLE 10

The procedure described in Example 2 is repeated except that N-(3-trimethylstannylpropen-2-yl)-2β-carbomethoxy-3β-(4-chlorophenyl)tropane is used instead of trimethylstannyl-β-CT.

EXAMPLE 11

The procedure described in Example 2 is repeated except that N-(3-trimethylstannylpropen-2-yl)-2β-carbomethoxy-3β-(4-fluorophenyl)tropane is used instead of trimethylstannyl-β-CT.

The increased yield due to the presence of a catalytically effective amount of chloride anion at very high activity levels on the order of 560 mCi is demonstrated in Examples 12–14. As shown in a comparison of Examples 13 and 14, the presence of the chloride anion resulted in a thirteen-fold increase in the yield from 5% yield to 64% yield.

EXAMPLE 12

Into a vial was placed 30 mCi of no-carrier-added sodium iodide ($^{123}$I) in dilute sodium hydroxide (36 μL). Trimethylstannyl-β-CT (50 μg) was dissolved in ethanol (800 μL). 100 μL of 1N sodium chloride was added to the sodium iodide, followed by the ethanol mixture, then 170 μL of a dilute solution of peracetic acid (0.06 μL/mL) in 7.2N sulfuric acid. The mixture was stirred for 90 seconds, and quenched by the addition of sodium bisulfite solution. The formation of $^{123}$I β-CIT was monitored by thin layer chromatography (ITLC–SG, eluted with ethanol:water:acetic acid, 20:80:2.5 v/v/v). The yield of $^{123}$I β-CIT was 99%.

EXAMPLE 13

The procedure described in Example 12 was repeated exactly as described except that the 30 mCi of sodium iodide was replaced by 559 mCi (714 μL). The yield of $^{123}$I β-CIT as determined by the ITLC method was 64%.

EXAMPLE 14

The procedure described in Example 12 was repeated exactly as described except that the 30 mCi of sodium iodide was replaced by 555 mCi (709 μL) and the 100 μL of 1N sodium chloride was omitted. The yield of $^{123}$I β-CIT as determined by the ITLC method was 5%.

As shown in the following Examples 15 and 16, the catalytic anion's beneficial effect on the yield of the radiopharmaceutical extends to aged radiolabels, i.e. those manufactured in advance rather than at the time of preparation of the radiopharmaceutical.

EXAMPLE 15

32% peracetic acid was diluted 33,333 times in water to obtain a 0.03 μL/mL solution. 50 μL of 5N sulphuric acid and 100 μL water was added to 100 μL of 370 mCi/mL no-carrier-added sodium iodide ($^{123}$I) (the $^{123}$I had been manufactured the day before). To this mixture was added 50 μL of the 0.03 μL/mL peracetic acid solution and 200 μL of a 33.3 μg/mL trimethylstannyl-β-CT solution in acetonitrile.

The reagents were mixed. After 5 minutes, the reaction was quenched by the addition of 20 μL of 1mg/mL sodium bisulphite. The formation of $^{123}$I-β-CIT was monitored by HPLC (column: C-18 μ-Bondapak; solvent: 2.68 g of ammonium chloride in 600 mL of water and 400 mL of acetonitrile; sample: 20 μl). The yield of $^{123}$I-β-CIT was 72.4%.

EXAMPLE 16

The procedure described in Example 15 was repeated exactly as described, except that 100 μL of 2.5M sodium chloride was added to the sodium iodide ($^{123}$I) instead of 100 μL of water. The yield of $^{123}$I-β-CIT was 91.7%.

The following series of examples, together with the above examples, examined the effect of other anions. The overall conclusions is that the catalytic effect appears to be bromide>chloride>nitrite. All experiments were performed once using "aged" iodide (Examples 12–21) and repeated using fresh $^{123}$I (Examples 22–28). See Table I for a tabulation of these results. The difference between "fresh" and "aged" iodide appears to be due to the activity level being higher in "fresh" than in "aged".

EXAMPLE 17

The procedure described in Example 15 was repeated exactly as described, except that 100 μL of 2.5 M potassium bromide was added to the sodium iodide ($^{123}$I) instead of 100 μL of water. The yield of $^{123}$I-β-CIT was 99.0%.

EXAMPLE 18

The procedure described in Example 15 was repeated exactly as described, except that 100 μL of 2.5M sodium fluoride was added to the sodium iodide ($^{123}$I) instead of 100 μL of water. The yield of $^{123}$I-β-CIT was 41.2%.

EXAMPLE 19

The procedure described in Example 15 was repeated exactly as described, except that 100 μL of 2.5 M potassium thiocyanate (KSCN) was added to the sodium iodide ($^{123}$I) instead of 100 μL of water. The yield of $^{123}$I-β-CIT was 82.0%.

EXAMPLE 20

The procedure described in Example 15 was repeated exactly as described, except that 100 μL of 2.5M sodium nitrite was added to the sodium iodide ($^{123}$I) instead of 100 μL of water. The yield of $^{123}$I-β-CIT was 87.3%.

EXAMPLE 21

The procedure described in Example 15 was repeated exactly as described, except that 100 μL of 2.5M sodium nitrate was added to the sodium iodide ($^{123}$I) instead of 100 μL of water. The yield of $^{123}$I-β-CIT was 42.2%.

EXAMPLE 22

The procedure described in Example 15 was repeated exactly as described, except that a fresh batch of sodium iodide ($^{123}$I) was used, with a radioactive concentration of 1127 mCi/mL. The yield of $^{123}$I-β-CIT was 41.1%.

EXAMPLE 23

The procedure described in Example 22 was repeated exactly as described, except that 100 μL of 2.5 M sodium chloride was added to the sodium iodide ($^{123}$I) instead of 100 μL of water. The yield of $^{123}$I-β-CIT was 96.4%.

EXAMPLE 24

The procedure described in Example 22 was repeated exactly as described, except that 100 μL of 2.5M potassium bromide was added to the sodium iodide ($^{123}$I) instead of 100 μL of water. The yield of $^{123}$I-β-CIT was 98.5%.

EXAMPLE 25

The procedure described in Example 22 was repeated exactly as described, except that 100 μL of 2.5M sodium fluoride was added to the sodium iodide ($^{123}$I) instead of 100 μL of water. The yield of $^{123}$I-β-CIT was 1.4%.

EXAMPLE 26

The procedure described in Example 22 was repeated exactly as described, except that 100 μL of 2.5M sodium iodide ($^{123}$I) instead of 100 μL of water. The yield of $^{123}$I-β-CIT was 68.4%.

EXAMPLE 27

The procedure described in Example 22 was repeated exactly as described, except that 100 μL of 2.5M sodium nitrite was added to the sodium iodide ($^{123}$I) instead of 100 μL of water. The yield of $^{123}$I-β-CIT was 58.0%.

EXAMPLE 28

The procedure described in Example 22 was repeated exactly as described, except that 100 μL of 2.5M sodium iiodide ($^{123}$I) instead of 100 μL of water. The yield of $^{123}$I-β-CIT was 67.7%.

The following Table, Table I, shows the yields of $^{123}$I β-CIT using various anions as catalysts

TABLE I

| | "Aged" $^{123}$I | |
| --- | --- | --- |
| anion | Example # | % yield |
| none | 15 | 72.4 |
| chloride | 16 | 91.7 |
| bromide | 17 | 99.0 |
| fluoride | 18 | 41.2 |
| thiocyanate | 19 | 82.0 |
| nitrite | 20 | 87.3 |
| nitrate | 21 | 42.2 |

| | Fresh $^{123}$I | |
| --- | --- | --- |
| anion | Example # | % yield |
| none | 22 | 41.1 |
| chloride | 23 | 96.4 |
| bromide | 24 | 98.5 |
| fluoride | 25 | 1.4 |
| thiocyanate | 26 | 68.4 |
| nitrite | 27 | 58.4 |
| nitrate | 28 | 67.7 |

We have also discovered that the bromide anion has a better catalytic effect than the chloride anion, which in turn has a better catalytic effect than the nitrite anion. Examples 29 and 30 demonstrate this difference.

EXAMPLE 29

32% percetic acid was diluted 16,667 times in 7.2N sulphuric acid to obtain a 0.06 μL/mL solution. 25 μL of 1M sodium chloride and 42 µL of water was added to 225 µL of 889 mCi/mL no-carrier-added sodium iodide ($^{123}$I). To this mixture was added 200 µL of 62.5 µg/mL of trimethylstannyl-β-CT solution in acetonitrile and 42 µL of the 0.06 µL/mL peracetic acid solution. The reagents were mixed. After 90 seconds, the reaction was stopped by the addition of 25 µL of 1mg/mL sodium bisulphite. The formation of $^{123}$I-β-CIT was monitored by thin layer chromatography (ITLC-SG, eluted with ethanol:water:acetic acid 20:80:2.5 v/v/v). The yield of $^{123}$I-β-CIT was 31.7%.

EXAMPLE 30

The procedure described in example 29 was repeated exactly as described, except that 25 µL of 1 M potassium bromide was added to the sodium iodide ($^{123}$I) instead of 25 µL of sodium chloride. The yield of $^{123}$I-β-CIT was 96.1%.

From the foregoing description, one skilled in the art can easily ascertain the essential characteristics of the invention and, without departing from the spirit and scope thereof, can make various changes and modifications of the invention and adapt it to various usages and conditions.

What is claimed is:

1. A process for the preparation of a radiopharmaceutical by destannylation of a trialkyl tin substituted precursor with a radioactive halogen composition in the presence of a catalyst selected from the group comprising bromide, chloride and nitrite anions.

2. The process of claim 1 wherein said radioactive halogen is radioactive iodine, radioactive astatine, or radioactive bromine.

3. The process of claim 2 wherein said radioactive halogen composition is selected from the group consisting of $^{123}$I, $^{124}$I, $^{125}$I, $^{131}$I, $^{211}$At, and $^{77}$Br.

4. The process of claim 1 wherein the catalyst is present in concentrations from about 0.01 N to about 1.0 N in the reaction mixture.

5. The process of claim 1 wherein a trialkyl tin radical on the trialkyl tin precursor has the following formula:

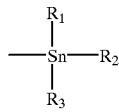

wherein $R_1$, $R_2$, and $R_3$ are independently straight or branched alkyl groups having from one to six carbon atoms.

6. The process of claim 5, wherein $R_1$, $R_2$, and $R_3$ are independently selected from the group consisting of methyl, ethyl, n-propyl, isopropyl, n-butyl, sec-butyl, isobutyl, tert-butyl, n-pentyl, and n-hexyl.

7. The process of claim 1 wherein said destannylation is conducted in an acid medium.

8. The process of claim 7 wherein said acid medium is formed by the addition of sulfuric acid or acetic acid.

9. The process of claim 1 wherein said radiopharmaceutical is a $^{123}$I labeled cocaine analog.

10. The process of claim 1 wherein said radiopharmaceutical is $^{123}$I β-CIT.

11. The process of claim 1 wherein said radiopharmaceutical is $^{123}$I β-CIT-FP $^{123}$I-2β-carbomethoxy-3β-(4-iodophenyl)-N-(3-fluoropropyl)nortropane.

12. A process for the preparation of a radiopharmaceutical from a trialkyl tin substituted precursor comprising the steps of:

forming a solution of said trialkyl tin substituted precursor in a solvent;

adding a radioactive halogen composition to the solution of the trialkyl tin substituted precursor;

adding a catalytically effective amount of an anion selected from the group comprising bromide, chloride and nitrite anion to the radioactive halogen composition and trialkyl tin substituted precursor solution to form a reaction mixture;

acidifying said reaction mixture;

adding an oxidizing agent to the acidified reaction mixture and allowing it to react to produce said radiopharmaceutical.

13. The process of claim 12 wherein the said chloride anion is present in concentrations from about 0.01 N to about 1.0 N in the reaction mixture.

14. The process of claim 12 wherein a trialkyl tin radical on the trialkyl tin precursor has the following formula:

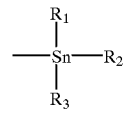

wherein $R_1$, $R_2$, and $R_3$ are independently straight or branched alkyl groups having from one to six carbon atoms.

15. The process of claim 14, wherein $R_1$, $R_2$, and $R_3$ are independently selected from the group consisting of methyl, ethyl, n-propyl, isopropyl, n-butyl, sec-butyl, isobutyl, tert-butyl, n-pentyl, and n-hexyl.

16. The process of claim 12 wherein said radioactive halogen composition contains radioactive iodine, radioactive astatine, or radioactive bromine.

17. The process of claim 16 wherein said radioactive halogen composition is selected from the group consisting of $^{123}$I, $^{124}$I, $^{125}$I, $^{131}$I, $^{211}$At, and $^{77}$Br.

18. The process of claim 12 wherein the reaction mixture is acidified by the addition of sulfuric acid or acetic acid.

19. The process of claim 12 wherein said radiopharmaceutical is a $^{123}$I labeled cocaine analog.

20. The process of claim 12 wherein said radiopharmaceutical is $^{123}$I β-CIT.

21. The process of claim 12 wherein said radiopharmaceutical is $^{123}$I β-CIT-FP $^{123}$I-2β-carbomethoxy-3β-(4-iodophenyl)-N-(3-fluoropropyl)nortropane.

22. A process for reducing the effects of radiolysis on the yield of a high activity radiopharmaceutical produced by halogenodestannylation of a trialkyl tin substituted precursor with a high activity radiohalogen, said process comprising the steps of:

a. forming a solution of said trialkyl tin substituted precursor in a solvent;

b. adding a high activity radioactive halogen composition to the solution of the trialkyl tin substituted precursor;

c. adding a catalytically effective amount of an anion selected from the group comprising bromide, chloride and nitrite anion to the high activity radioactive halogen composition and trialkyl tin substituted precursor solution to form a reaction mixture;

d. acidifying said reaction mixture; and e. adding an oxidizing agent to the acidified reaction mixture and allowing it to react to produce said high activity radiopharmaceutical wherein said catalytically effective amount of anion reduces the effect of radiolysis and increases the yield of said high activity radiopharmaceutical.

23. The process of claim 22 wherein the catalytically effective amount of anion is present in concentrations from about 0.01 N to about 1.0 N in the reaction mixture.

24. The process of claim 22 wherein said high activity radioactive halogen composition contains radioactive iodine, radioactive astatine, or radioactive bromine.

25. The process of claim 24 wherein said high activity radioactive halogen composition is selected from the group consisting of $^{123}$I, $^{124}$I, $^{125}$I, $^{131}$I, $^{211}$At, and $^{77}$Br.

26. The process of claim 22 wherein said radioactive halogen is at least 100 mCi.

27. The process of claim 22 wherein a trialkyl tin radical on the trialkyl tin precursor has the following formula:

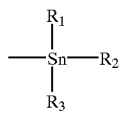

wherein $R_1$, $R_2$, and $R_3$ are independently straight or branched alkyl groups having from one to six carbon atoms.

28. The process of claim 27, wherein $R_1$, $R_2$, and $R_3$ are independently selected from the group consisting of methyl, ethyl, n-propyl, isopropyl, n-butyl, sec-butyl, isobutyl, tert-butyl, n-pentyl, and n-hexyl.

29. The process of claim 22 wherein the reaction mixture is acidified by the addition of sulfuric acid or acetic acid.

30. The process of claim 22 wherein said radiopharmaceutical is a $^{123}$I labeled cocaine analog.

31. The process of claim 22 wherein said radiopharmaceutical is $^{123}$I β-CIT.

32. The process of claim 22 wherein said radiopharmaceutical is $^{123}$I β-CIT-FP $^{123}$I-2β-carbomethoxy-3β-(4-iodophenyl)-N-(3-fluoropropyl)nortropane.

33. A process for increasing the yield of a radiopharmaceutical prepared by destannylation of a trialkyl tin substituted precursor with a radioactive halogen composition wherein said process is conducted in the presence of a catalyst selected from the group comprising bromide, chloride and nitrite anions.

* * * * *